United States Patent [19]

Wiele

[11] Patent Number: 5,061,180

[45] Date of Patent: Oct. 29, 1991

[54] DENTAL INSTRUMENT

[76] Inventor: Gary B. Wiele, 950 Francis Pl., Suite 311, Clayton, Mo. 63105

[21] Appl. No.: 345,283

[22] Filed: May 1, 1989

[51] Int. Cl.⁵ .................. A61C 17/06; A61C 17/14
[52] U.S. Cl. ......................... 433/91; 433/95; 604/902
[58] Field of Search ............ 433/91, 95, 81, 80, 433/85, 84; 604/902, 33, 34, 35

[56] References Cited

U.S. PATENT DOCUMENTS

| | | | |
|---|---|---|---|
| 2,255,657 | 9/1941 | Freedman | 433/91 X |
| 3,208,145 | 9/1965 | Turner | 433/95 |
| 3,453,735 | 7/1969 | Burt | 433/96 |
| 3,460,255 | 8/1969 | Hutson | 433/91 |
| 3,570,483 | 3/1971 | Straum | 433/80 X |
| 3,593,423 | 7/1971 | Jones | 32/22 |
| 3,624,907 | 12/1971 | Brass et al. | 433/91 X |
| 3,889,675 | 6/1975 | Stewart | 604/34 |
| 4,213,243 | 7/1980 | Flatland | 433/82 X |
| 4,249,899 | 2/1981 | Davis | 433/80 X |
| 4,253,831 | 3/1981 | Eaton II | 433/91 |
| 4,340,365 | 7/1982 | Pisanu | 433/91 X |
| 4,397,640 | 8/1983 | Haug et al. | 433/95 X |
| 4,487,600 | 12/1984 | Brownlie et al. | 604/35 |
| 4,526,573 | 7/1985 | Lester et al. | 433/95 X |
| 4,531,913 | 7/1985 | Taguchi | 433/80 |
| 4,672,953 | 6/1987 | DiVito | 433/91 X |
| 4,872,837 | 10/1989 | Issalene et al. | 433/91 X |
| 4,878,900 | 11/1989 | Sundt | 433/91 X |
| 4,883,426 | 11/1989 | Ferrer | 433/91 |

FOREIGN PATENT DOCUMENTS 2058576  4/1981  United Kingdom .................. 433/95

Primary Examiner—Robert P. Swiatek
Assistant Examiner—Nicholas A. Lucchesi
Attorney, Agent, or Firm—Rogers, Howell & Haferkamp

[57]        ABSTRACT

A dental instrument has first stationary and second rotatable tube sections with the rotatable tube section being press fit in the stationary tube section to provide a rotatable and releasable connection between the two tube sections. Stationary and rotatable conduits extend along the sides of the stationary and rotatable tube sections repsectively and are positioned concentric to their respective tube sections at the point of connection between the tubes to provide a rotatable and releasable connection between the stationary and rotatable conduits. A first manually operated valve varies the suction force through the stationary and rotatable tube sections. A second manually operated valve selectively supplies fluid under pressure from first and second fluid supply ducts through the stationary and rotatable conduits to produce a cleaning spray from the rotatable conduit. The pressure spray end of the rotatable conduit and the suction end of the rotatable tube section are provided with a beveled surface to facilitate positioning of the end of the dental instrument close to the work surface. The dental instrument is constructed of plastic and may be disposed of after each use rather than requiring sterilization of the instrument after each use.

20 Claims, 1 Drawing Sheet

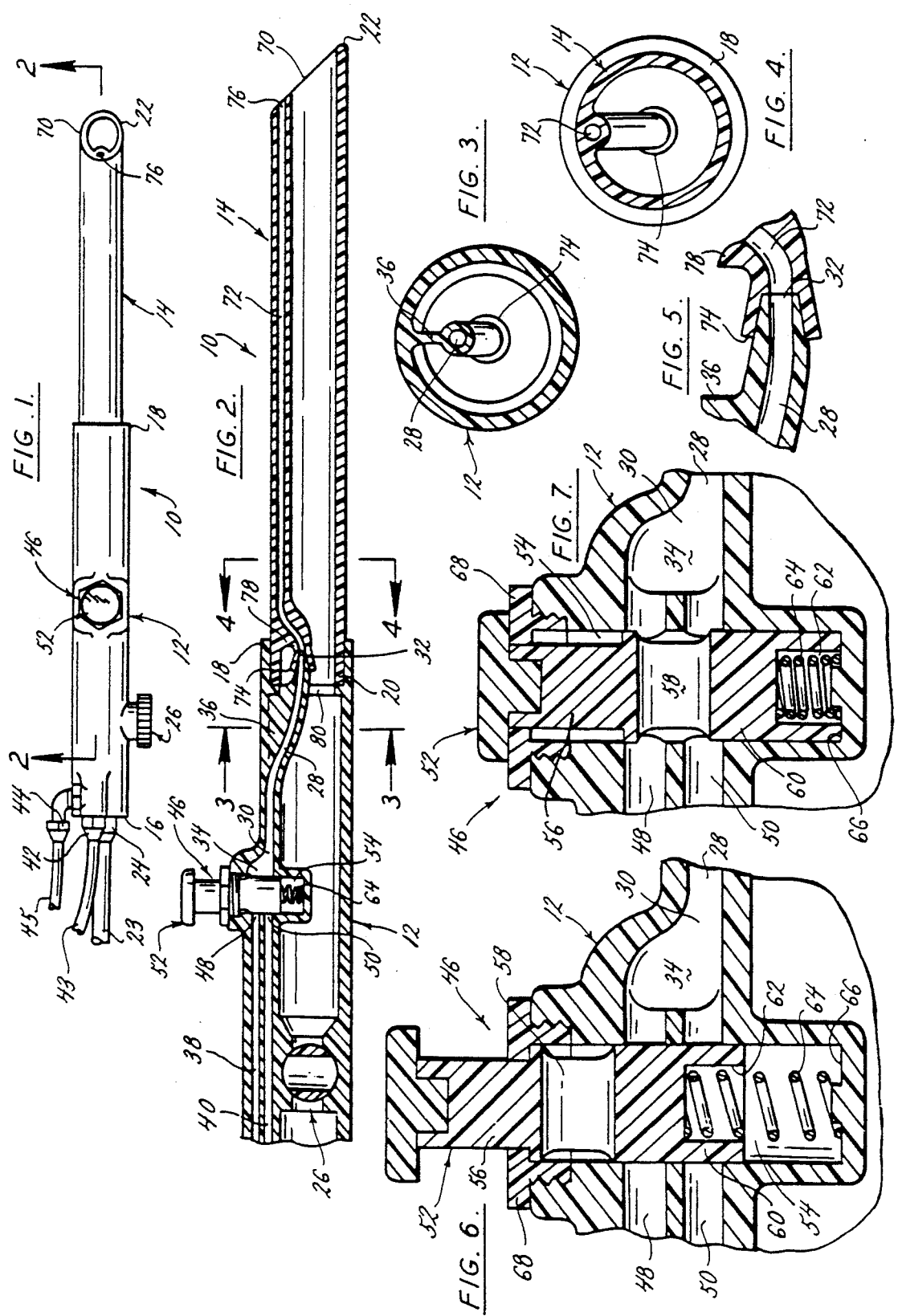

DENTAL INSTRUMENT

BACKGROUND OF THE INVENTION (1) Field of the Invention

This invention relates to hand held dental instruments that provide suction and selectively provide a pressurized spray of air and water. In particular, this dental instrument incorporates a suction tube having a rotatable, beveled, end that provides both a directional suction, and provides for selective spraying of water, air, or both from the end of the tube.

(2) Description of the Related Art

In a standard dentist's office the equipment usually includes a separate suction system having a hose connected to a suction tube that is hand held and manipulated to remove substances from and clear areas of a patient's mouth. This suction tube is commonly provided with a beveled end to provide a greater suction when the tube is held at an angle with the beveled end parallel to the work surface.

The standard dentist's office also includes a water and air system incorporating a discharge tube. The discharge tube is hand held and a manually operated valve on the discharge tube is selectively operable to direct air, water, or a combined air-water spray to different locations in the patient's mouth.

It is often necessary for a dental person (dentist, hygienist, or dental assistant) to use the air-water discharge tube to clear away an area of the patient's mouth where work is being performed while simultaneously using the suction tube to remove the sprayed water and other substances from the patient's mouth. This requires the dental person to use both his hands for cleaning and clearing away the surface, one hand operating the discharge tube and one hand operating the suction tube, leaving neither hand free to perform other functions. It is often necessary to clear away an area of the patient's mouth where the dentist is working with a dentistry tool. While using one hand to operate the vacuum, the dental person must use his other hand to blow or spray the area. If a dentist is working alone, he must put down the "dentistry tool" and use both hands to clear the field then pick up the dentistry tool to work again. These repeated motions are a great inconvenience to the dentist, they slow down the work being performed, and can cause discomfort to the patient.

Decontamination and good hygiene practices are of great importance to prevent germ, infection, and disease transfer between patients and between a patient and a dental person. The conventional spray tubes presently used are expensive to manufacture and therefore are not readily disposable after each use. Therefore, the spray tube devices should be sterilized by the dentist after each use. Because of the inconvenience of sterilizing the spray tube, many may neglect this phase of decontamination.

The present invention overcomes the above-listed shortcomings of the conventional instruments by providing a unique, single instrument that can be held in one hand and easily manipulated and operated by the dental person, that produces both a suction and a selectively operated discharge of air or air and water, and is also disposable after each use.

It is therefore an object of the present invention to provide an improved dental instrument having a rotatable suction tube with beveled end that enables the operator to orient the suction opening of the instrument at selected positions in a patient's mouth, and also provides a selective spray of air, water, or both through a discharge tube that extends through the suction tube.

SUMMARY OF THE INVENTION

This dental instrument comprises two coextensive suction tube sections that are rotatably connected together end to end to form a composite suction tube. A coupling end of one of the tube sections is press fitted into a complimentary coupling end of the other tube section to provide a friction coupling between the two tube sections that permits relative rotation making one tube section stationary and the other rotatable about their common axis. A flexible hose or tube leading from a suitable vacuum source is connected to the stationary tube section. The free end of the rotatable tube section defines a beveled suction inlet. A manual valve is provided in the stationary tube section to selectively vary the level of vacuum through the corporate suction tubes. A discharge conduit extends through the interior of the suction tube. The discharge conduit has a discharge outlet that is located at the suction tube inlet. Manually operated valves are provided on the stationary suction tube to adjust the suction magnitude and to selectively supply pressurized air and/or water to the discharge conduit.

The two discharge conduit sections are coaxial and an end of one section fits into a complimentary end of the other section. When the coupling ends of the tube sections are brought together, the complimentary ends of the conduit sections are press fitted together to form a rotatable fluid connection between the two conduit sections. Thus one conduit section remains stationary with the stationary tube section and the other conduit section rotates with the rotatable tube section.

Two flexible supply ducts are connected to the stationary tube section. These supply ducts are adapted to be connected respectively to a source of pressurized air and to a source of pressurized water.

An additional manual valve is provided on the stationary tube section. Operation of the additional manual valve selectively supplies air, water, or both to the discharge conduit.

The rotatable suction tube section is constructed of injection molded plastic and may be disposed of after its use or depending on the type of thermoplastic would be steam heat autoclaved and reused. The stationary tube section may also be constructed of an injection molded plastic and may also be disposable after each use.

Another important advantage of this invention is that, because of the proximity of the discharge tube to the suction tube, splatter is reduced and is confined to the suction area. This reduces the risk of disease transmission between the patient and a dental person.

Decontamination is further made easy because of the disposability of both the suction and discharge tubes. Since disposal and replacement are quick, decontamination time is reduced with corresponding economy.

BRIEF DESCRIPTION OF THE DRAWINGS

Further objects and features of the present invention are revealed in the following detailed description of the preferred embodiment of the invention and in the drawing figures wherein:

FIG. 1 is a top plan view of the suction tube instrument of the present invention;

FIG. 2 is a side elevation view in section of the instrument of the present invention taken along line 2—2 of FIG. 1;

FIG. 3 is a side elevation view in section taken along line 3—3 of FIG. 2;

FIG. 4 is a side elevation view in section taken along line 4—4 in FIG. 2;

FIG. 5 is a side elevation view in section of the detail of the male/female coupling between the first and second conduits of the present invention;

FIG. 6 is a side elevation view in section of the detail of the valve structure of the stationary tube section in a first position of the valve;

FIG. 7 is side elevation view in section of the detail of the valve structure in the stationary tube section for a second position of the manual valve.

DESCRIPTION OF THE PREFERRED EMBODIMENT

The dental instrument 10 of the invention comprises a first stationary tube section 12 and a second rotatable tube section 14. The first stationary tube section 12 has first and second ends 16, 18 respectively. The rotatable tube section 14 has first and second ends 20, 22 respectively.

The first end 16 of the stationary tube section 12 of the instrument is adapted to be connected to a source of vacuum pressure in any manner known in the art. FIG. 1 shows the first end 16 of the stationary tube 12 connected to a vacuum hose 23 by a threaded coupling 24. A first manually adjustable valve assembly 26 is provided in the stationary tube section 12. The first valve assembly 26 is arranged to be manually rotated through 90° of rotation by the operator to adjust the valve between a fully closed position and a fully open position to vary the vacuum pressure in the stationary tube section 12.

A first section of a fluid discharge conduit 28 is also provided in the stationary tube section 12. The stationary discharge conduit 28 has first and second ends 30, 32 respectively. The second end 32 of the stationary discharge conduit 28 is concentric to the stationary tube section 12 in the area of the second end 18 of the tube. The stationary conduit 28 gradually curves from its second end 32, positioned concentric to the second end 18 of the stationary tube section 12, toward its first end 30 positioned at the side of the stationary tube section 12. The first end 30 of the stationary conduit 28 terminates in a mixing chamber 34 on the side of the stationary tube section 12.

A webb member 36 extends between the second end 32 of the stationary discharge conduit 28 and the interior wall of the stationary tube section and supports the second end 32 of the stationary discharge conduit 28 in its concentric position. Although only 1 webb member 36 is shown in the drawing figures, additional webb members may be provided angularly spaced around the second end 32 of the stationary discharge conduit 28 to provide additional support to the conduit.

First and second fluid pressure supply ducts 38, 40 are provided on the side of the stationary tube section 12. The input ends 42, 44 of the respective first and second fluid pressure supply ducts 38, 40 are adapted to be connected to two separate sources of fluid pressure such as pressurized air and pressurized water. The supply ducts may be connected to the sources of fluid pressure in any manner known in the art and are shown being connected by threaded fasteners to two fluid supply hoses 43, 45 in the drawings.

A second valve assembly 46 is provided on the stationary tube section 12. The second valve assembly 46 is manually operated and provides selective communication between the output ends 48, 50 of the respective first and second fluid pressure supply ducts 38, 40 and the mixing chamber 34. The second valve assembly 46 is shown in FIGS. 6 and 7 and comprises a valve spool 52 slidably received in a valve cylinder 54. The valve spool 52 is divided into three sections including a manual plunger section 56, a fluid bypass section 58, and a fluid interrupt section 60. A bore hole 62 coaxial to the spool 52 is provided in the end of the spool adjacent the fluid interrupt section 60. A biasing spring 64 is positioned in the bore hole 62 between the fluid interrupt section 60 of the valve spool 52 and the bottom 66 of the valve cylinder 54. The biasing spring 64 biases the valve spool 52 in an upward direction as viewed in FIGS. 2, 6 and 7. A valve cylinder cap 68 is provided at the top of the valve cylinder 54 as viewed in FIGS. 6 and 7 to retain the valve spool 52 in the valve cylinder 54. As seen in FIGS. 6 and 7, the output ends 48, 50 of the respective first and second supply ducts 38, 40 connect with one side of the valve cylinder 54, and the mixing chamber 34 connects with the opposite side of the valve cylinder 54 opposite the output ends 48, 50 of the respective first and second supply ducts 38, 40.

The first end 20 of the rotatable tube 14 is adapted to be press fit into the second end 18 of the stationary tube 12 to provide a rotatable, fluid-tight connection between the tubes as best seen in FIG. 2. The outer diameter of the first end 20 of the rotatable tube 14 is dimensioned to be press fit inside the interior diameter of the second end 18 of the stationary tube 12 to provide the fluid-tight friction connection. The friction connection between the stationary and rotatable tube sections 12, 14 permits the rotatable tube section 14 to be rotated relative to the stationary tube section 12. The second end 22 of the rotatable tube 14 is beveled to enable the operator to create an increased suction into the rotatable tube 14 by positioning the beveled surface 70 parallel to the surface to be cleaned. As best seen in FIG. 2, the beveled surface 70 at the second end 22 of the tube produces a side of the tube having a short relative length opposite the side of the tube having a long relative length.

A rotatable discharge conduit 72 having first and second ends 74, 76 respectively, extends through the rotatable tube section 14. The first end 74 of the rotatable discharge conduit 72 is positioned concentric to the first end 20 of the rotatable tube section 14, and the second end 76 of the discharge conduit 72 is positioned adjacent the short side of the rotatable tube section 14 and is generally aligned with the beveled second end 22 of the rotatable tube section 14.

A second webb member 78 extends between the first end 74 of the rotatable discharge conduit 72 and the first end 20 of the rotatable tube section 14 and supports the first end 74 of the rotatable conduit concentric to the first end 20 of the rotatable tube section 14. Although only one second webb member is disclosed in the preferred embodiment, additional webb members providing additional support to the first end 74 of the rotatable discharge conduit 72 may be employed without departing from the scope of the invention. In the area of the first end 74 of the rotatable discharge conduit 72, the discharge conduit 72 gradually curves toward the side wall of the rotatable tube section 14 having the shorter relative length, and then runs along the side wall of the rotatable tube section 14 to the second end 22 of the rotatable tube 14.

The second end 32 of the stationary discharge conduit 28 is configured as a male coupling member. The first end 74 of the rotatable discharge conduit 72 is configured as a female coupling member arranged to receive the second end 32 of the stationary discharge conduit 28 when the first end 20 of the rotatable tube section 14 is press fit into the second end 18 of the stationary tube section 12. An abutment ring 80 inside the second end 18 of the stationary tube 12 limits the extent to which the rotatable tube section 14 can be inserted into the second end 18 of the stationary tube section 12. The first end 20 of the rotatable tube section 14 just contacts the abutment ring 80 when the second end 32 of the stationary discharge conduit 28 is completely nested in the first end 74 of the rotatable discharge conduit 72. The abutment ring 80 prevents damaging the second and first ends 32, 74 of the respective stationary and rotatable conduits 28, 72 by preventing the insertion of the first end 20 of the rotatable tube section 14 too far into the second end 18 of the stationary tube section 12.

In operation, the first end 20 of the rotatable tube section 14 is press fitted into the second end 18 of the stationary tube section 12 and rotated by the operator relative to the stationary tube section 12 to position the bevel surface 70 at the second end 22 of the rotatable tube section 14 at a desired inclination.

Following the orientation of the beveled end 70, the operator then rotates the first valve assembly 26 from its fully closed position shown in FIG. 2 through 90° to its fully opened position, or through some lesser degree of rotation to set the desired suction through the stationary and rotatable tube sections 12, 14. With the first valve assembly 26 open to the desired extent, the suction tube dental instrument 10 may be used by the operator to remove substances from the mouth of the patient by the vacuum force at the beveled end 70 of the rotatable tube section 14.

In the at rest position of the second valve assembly 46 shown in FIGS. 2 and 6, first and second pressurized fluids delivered to the first and second fluid pressure supply ducts 38, 40 respectively are not communicated to the stationary and rotatable conduits 28, 72, and the instrument 10 functions only as a vacuum source. In this position of the valve spool 52, the fluid interrupt section 60 of the spool prevents fluid communication between the first and second fluid pressure supply ducts 38, 40 respectively, and the mixing chamber 34. On manual depression of the manual plunger section 62 of the valve spool 52, the valve spool 52 moves axially downward against the bias of spring 64 as viewed in FIG. 6. In the first depressed position of the valve spool 52, intermediate the at rest position and the fully depressed position, the fluid bypass section 58 of the valve spool communicates the first fluid pressure supply duct 38 with the mixing chamber 34. This communicates the first fluid pressure in the first fluid pressure supply duct 38 with the mixing chamber 34, the stationary fluid discharge conduit 28, and the rotatable fluid discharge conduit 72 and sprays the first fluid from the second end 76 of the rotatable fluid discharge conduit 72. The pressurized first fluid may be air or water depending on the operator's preference of the pressurized fluid source connected to the first supply duct 38. When the valve spool 52 is fully depressed to its second depressed position, the fluid bypass section 58 of the valve spool 52 communicates both the first and second fluid pressure supply ducts 38, 40 with the mixing chamber 34. This permits the first and second pressurized fluids to flow through the first and second fluid supply ducts 38, 40, the mixing chamber 34, the stationary fluid discharge conduit 28, the rotatable fluid discharge conduit 72, and a mixture of the first and second pressurized fluids is sprayed from the second end 76 of the rotatable conduit 72. By selective operation of the second valve assembly 46, the operator of the instrument 10 can selectively stop the spray of pressurized fluids from the second end 76 of the rotatable conduit 72, can spray only the first pressurized fluid from the second end 76 of the rotatable conduit 72, or can spray a mixture of the first and second pressurized fluids from the second end 76 of the rotatable conduit 72. By choosing which of the first and second fluid pressure supply ducts 38, 40 will be connected to the pressurized air source and the pressurized water source, the operator can determine which of the two pressurized fluids will be sprayed from the second end 76 of the rotatable conduit 72 when the valve spool 52 is pressed to its first depressed position intermediate the at rest position and fully depressed positions.

Although a specific three position valve has been disclosed in describing the preferred embodiment of the invention, it should be apparent to those skilled in the art that various different types of valve assemblies employing one or more manual operating devices may be employed in the suction tube dental instrument 10 without departing from the scope of the present invention. It should also be apparent that various valve structures may be employed which selectively supply either first or second fluids or a mixture of these fluids to the second end 76 of the rotatable conduit 72 without departing from the scope of the present invention.

The preferred embodiment of the instrument has been described as being constructed of injection molded plastic. However, other materials such as stainless steel may be employed in constructing the stationary and rotatable conduits, with the conduits being molded into the injection molded stationary and rotatable tubes. In addition, materials other than plastic may be used in constructing the first and second valve assemblies, and the connections of the stationary tube section and the first and second fluid pressure supply ducts to the respective vacuum pressure source and the sources of first and second pressurized fluids.

While the present invention has been described with reference to a specific embodiment, it should be understood that modifications, and variations of the invention may be constructed without departing from the scope of the invention defined in the following claims.

What is claimed is:

1. A dental instrument comprising:
a first tube section having an interior bore and first and second ends, said first end of said tube being adapted to be connected to a vacuum pressure source;
a second tube section having an interior bore and first and second ends, one of said first end of said second tube section and said second end of said first tube section being press fit into frictional engagement with the other of said first end of said second tube section and said second end of said first tube section;

a first conduit separate from said interior bore of said first tube section and extending through the first tube section, said first conduit having first and second ends; and a second conduit separate from said interior bore of said second tube section and extending through said second tube section, said second conduit having first and second ends, said first end of said second conduit and said second ed of said first conduit being connected together for rotation relative to each other.

2. The dental instrument of claim 1 comprising:

said second end of said second tube and said second end of said second conduit being beveled and generally aligned.

3. The dental instrument of claim 1 comprising:

said first end of said second tube being press fit into said second end of said first tube to form a releasable, friction connection that enables relative rotation between said first and second tubes.

4. The dental instrument of claim 1 comprising:

a web member extending between said first end of said second tube and said first end of said second conduit and supporting said first end of said second conduit concentric to said first end of said second tube.

5. The dental instrument of claim 1 comprising:

a web member extending between said second end of said first tube and said second end of said first conduit and supporting said second end of said first conduit concentric to said second end of said first tube.

6. The dental instrument of claim 1 comprising:

said second conduit curving to a side of said second tube proximate to said first end of said second conduit, and said second conduit extending along said side of said second tube between said curve and said second end of said second tube.

7. The dental instrument of claim 6 comprising:

said second end of said second tube being beveled creating a relatively short second tube side, said second conduit extending along said relatively short side of said second tube.

8. The dental instrument of claim 1 comprising:

said first conduit curving to a side of said first tube proximate to said second end of said first conduit, said first conduit extending along said side of said first tube between said curve and said first end of said first conduit.

9. The dental instrument of claim 1 comprising:

said second end of said first conduit being press fit into said first end of said second conduit to form a releasable, fluid connection that enables relative rotation between said first and second conduits.

10. The dental instrument of claim 1 comprising:

a valve means arranged in said first tube intermediate said first and second ends of said first tube, said valve means being arranged to selectively vary vacuum pressure at said second end of said first tube.

11. The dental instrument of claim 1 comprising:

a valve means connected to said first end of said first conduit and arranged to selectively supply fluid to said first conduit.

12. The dental instrument of claim 11 comprising:

a third conduit having first and second ends, said first end of said third conduit being adapted to be connected to a first fluid source and said second end of said third conduit being connected to said valve means.

13. The dental instrument of claim 12 comprising:

a fourth conduit having first and second ends, said firs end of said fourth conduit being adapted to be connected to a second fluid source and said second end of said fourth conduit being connected to said valve means.

14. The dental instrument of claim 13 comprising:

said valve means being a three position valve adapted to interrupt communication between said first conduit and said third and fourth conduits in a first position, to communicate said first conduit with said third conduit in a second position, and to communicate said first conduit with said third and fourth conduits in a third position.

15. The dental instrument of claim 1 comprising:

one of said first end of said second conduit and said second end of said first conduit being press fit into frictional engagement with the other of said first end of said second conduit and said second end of said first conduit, said press fit frictional engagement between said first end of said second tube section and said second end of said first tube section, and said press fit frictional engagement between said first end of said second conduit and said second end of said first conduit enabling said first tube section and said first conduit to rotate relative to said second tube section and said second conduit when oppositely directed torsional forces are exerted on said first and second tube sections respectively, and enabling said first tube section to be pulled and separated from said second tube section when oppositely directed axial forces are exerted on said first and second tube sections respectively.

16. A dental instrument comprising:

a first tube section having an interior bore and first and second ends;

a second tube section having an interior bore and first and second ends, one of said first end of said second tube section and said second end of said first tube section being press fit into frictional engagement with the other of said first end of said second tube section and said second end of said first tube section;

a first conduit separate from said interior bore of said first tube section and extending through said first tube section, said first conduit having first and second ends, said first end of said first conduit being positioned adjacent an interior side wall of said first tube section, and a second conduit separate from said interior bore of said second tube section and extending through said second tube section, said second conduit having first and second ends, said first end of said second conduit and said second end of said first conduit being connected together for rotation relative to each other, said second end of said second conduit being positioned adjacent an interior side wall of said second tube section.

17. The dental instrument of claim 16 comprising:

one of said first end of said second conduit and said second end of said first conduit being press fit into frictional engagement with the other of said first end of said second conduit and said second end of said first conduit, said press fit frictional engagement between said first end of said second tube section and said first tube section, and said press fit frictional engagement between said first end of said second conduit and said second end of said first conduit enabling said first tube section and said first conduit to rotate relative to said second tube section and said second conduit when oppositely directed torsional forces are exerted on said first and second tube sections respectively, and enabling said first tube section to be pulled and separated from said second tube section when oppositely directed axial forces are exerted on said first and second tube sections respectively.

18. A dental instrument comprising:
   a first tube section having an interior bore and first and second ends;
   a second tube section coaxial with said first tube section and having an interior bore and first and second ends, one of said first end of said second tube section and said second end of said first tube section being press fit into frictional engagement with the other of said first end of said second tube section and said second end of said first tube section;
   a first conduit separate from said interior bore of said first tube section and extending through said first tube section, said first conduit having first and second ends; and
   a second conduit separate from said interior bore of said second tube section and extending through said second tube section, said second conduit having first and second ends, said first end of said second conduit and said second end of said first conduit being connected together for rotation relative to each other.

19. The dental instrument of claim 18 comprising:
   one of said first end of said second conduit and said second end of said first conduit being press fit into frictional engagement with the other of said first end of said second conduit and said second end of said first conduit, said press fit frictional engagement between said first end of said second tube section and said second end of said first tube section, and said press fit frictional engagement between said first end of said second conduit and said second end of said fist conduit enabling said first tube section and said first conduit to rotate relative to said second tube section and said second conduit when oppositely directed torsional forces are exerted on said first and second tube sections respectively, and enabling said first tube section to be pulled and separated from said second tube section when oppositely directed axial forces are exerted on said first and second tube sections respectively.

20. A dental instrument comprising:
   a tubular body having an interior bore and first and second ends with first and second openings at said first and second ends, respectively;
   said first end of said body being adapted to be rotatably connected to a vacuum pressure source, enabling said body to be rotated relative to said vacuum pressure source;
   said first opening being positioned in a plane that is perpendicular to said tubular body at said first end;
   said second end of said body being beveled, creating a side portion of said tubular body that is shorter than a remaining portion of said tubular body;
   said second opening being positioned in a plane that is positioned at an angle to said tubular body at said second end; and
   a conduit having first and second ends extending through said body, said first end of said conduit being coplanar with said first end of said body and being concentric with said interior bore at said first end of said body, and said second end of said conduit being contiguous with said second end of said body at said side portion of said body that is shorter than the remaining portion of said body.

* * * * *